United States Patent [19]

Anderson et al.

[11] Patent Number: 5,296,362

[45] Date of Patent: Mar. 22, 1994

[54] MICROBIOLOGICAL PRODUCTION OF POLYESTERS HAVING $C_8$ AND/OR $C_{10}$ MONOMER REPEAT UNITS

[75] Inventors: Alistair J. Anderson, Hull; Edwin A. Dawes, Humberside; Geoffrey W. Haywood, Hull; David Byrom, Cleveland, all of England

[73] Assignee: Imperial Chemical Industries PLC, London, England

[21] Appl. No.: 507,842

[22] Filed: Apr. 12, 1990

[30] Foreign Application Priority Data

Apr. 12, 1989 [GB] United Kingdom ................. 8908214
May 19, 1989 [GB] United Kingdom ................. 8911577
Oct. 4, 1989 [GB] United Kingdom ................. 8922362

[51] Int. Cl.$^5$ .......................... C12P 7/62; C12P 1/00
[52] U.S. Cl. ...................................... 435/135; 435/41; 435/134; 435/146; 435/253.3
[58] Field of Search ............ 435/134, 135, 146, 253.3, 435/41

[56] References Cited

U.S. PATENT DOCUMENTS 3,121,669  2/1964  Baptist et al. ........................ 435/146
4,477,654 10/1984  Holmes et al. ........................ 435/135

FOREIGN PATENT DOCUMENTS 0114086  7/1984  European Pat. Off. .
0274151  7/1988  European Pat. Off. .

OTHER PUBLICATIONS de Smet et al, J. of Bacteriology, 154(2):870–878 (May, 1983).
Legeveen et al, Applied and Environmental Microbiology, 54(12):2924–2932 (Dec., 1988).
Brandl et al, Applied and Environmental Microbiology, 54(8):1977–1982 (Aug., 1988).
Haywood et al., Biotechnology Letters, 11(7):471–476 (1989).
Breed et al., Pseudomonadales/Pseudomonadaceae, Bergey's Manual of Determinative Bacteriology, Seventh Edition, 1957, pp. 99, 104–107, 112, 113.
Dando et al., Catalogue of Strains, The National Collections of Industrial and Marine Bacteria, 1990, pp. 108, 112, and 114.

Primary Examiner—Marian Knode
Attorney, Agent, or Firm—Cushman, Darby & Cushman

[57] ABSTRACT

A microbiological process, capable of producing polymers comprising monomer repeat units of the structure $$-O.CH((CH_2)_xCH_3).CH_2.-CO-$$

wherein x is particularly 6 from glucose, novel polymers produced through the process and new strains of Pseudomonas for use in the process.

2 Claims, No Drawings

MICROBIOLOGICAL PRODUCTION OF POLYESTERS HAVING $C_8$ AND/OR $C_{10}$ MONOMER REPEAT UNITS

BACKGROUND OF THE INVENTION

1. Field of Invention

The present invention relates to a microbiological process for the production of polymers, to novel polymers produced through such a process, and to microorganisms for use in such a process.

2. Description of Related Art

It is known that many bacteria are able to accumulate polymers, such as polymers of 3-hydroxybutyric acid (PHB), within their cells as an energy reserve material. For instance in EP-B-15669, PHB is produced through the aerobic culturing of certain strains of *Methylobacterium organophilum* on a substrate comprising methanol.

PHB is a straight chain polymer formed essentially from monomer repeat units having four carbon atoms having the structure

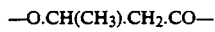

—O.CH(CH₃).CH₂.CO—

The term polymer hereinafter implies, unless stated otherwise, a straight chain polymer.

The monomer repeat unit from which PHB is formed is an example of a so-called C4 monomer.

Polymers have also been microbiologically produced, wherein at least some of the monomer repeat units have more than four carbon atoms. Thus in EP-A-69497, a process is disclosed wherein a polymer is formed comprising monomer repeat units of PHB in association with monomer repeat units having greater than four carbon atoms. The process involves cultivating a suitable microorganism, such as *Alcaligenes eutrophus* NCIB 11599, on a substrate comprising an organic acid that can be metabolised by the microorganism to the appropriate monomer repeat unit. (The abbreviations NCIB and NCIMB herein refer to the National Collections of Industrial and Marine Bacteria Ltd., PO Box 31, 135 Abbey Road, Aberdeen AB9 8DG, United Kingdom). For example, where the substrate is propionic acid, containing three carbon atoms, the microorganism synthesises monomer repeat unit of the form

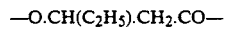

—O.CH(C₂H₅).CH₂.CO— the monomer repeat unit of the polymer of 3-hydroxyvaleric acid, having five carbon atoms, a so-called C5 monomer. Effectively, the microorganism can increase the number of carbon atoms present in the monomer repeat unit by two, over the number of carbon atoms present in the organic acid of the substrate.

De Smet et al, *Journal of Bacteriology*, May 1983, pp 870 to 878, have shown that poly-B-hydroxyoctanoate, a polymer formed essentially from monomer repeat units having eight carbon atoms, i.e. C8 monomers, is produced and accumulated by *Pseudomonas oleovorans* ATCC 29347, when the microorganism is cultivated on n-octane, i.e. a straight chain alkane. (The abbreviation ATCC herein refers to the American Type Culture Collection, 12301 Park Lawn Drive, Rockville, Md., 20852 USA).

Brandl et al, *Applied and Environmental Microbiology*, August 1988, pp 1977 to 1982, have further shown that polymers comprising monomer repeat units having up to eleven carbon atoms, i.e. C11 monomers, can be produced microbiologically. The microbiological process disclosed by Brandl et al involves the cultivation of *Pseudomonas oleovorans* ATCC 29347 on substrates comprising one of a number of different assimilable straight chain carbon compounds, such as alkanoic acids, alkanes and alkenes. It is shown that no polymer is produced unless an assimilable straight chain carbon compound having at least six carbon atoms is used in the substrate, and that the maximum yield of polymer occurs when an assimilable straight carbon compound having eight or nine carbon atoms is used.

Brandl et al also show that a trend exists such that the number of carbon atoms present in the monomer repeat units corresponds to the number of carbon atoms in the assimilable straight chain carbon compound used. Various monomer repeat units are shown to be produced which differ from one another by the number of carbon atoms contained therein. The number of carbon atoms present in some of the monomer repeat units are shown to differ by one to two from the number of carbon atoms present in the assimilable straight chain carbon compound. Where the assimilable straight chain carbon compound has fewer than ten carbon atoms the most common, i.e. modal, number of carbon atoms to be found in the monomer repeat unit is the same as the number of carbon atoms in the assimilable straight chain carbon compound. However, where the assimilable straight chain carbon compound contains ten carbon atoms this trend is not continued and less than 12 mol % of the monomer units have ten carbon atoms.

Thus, where the monomer repeat units are required to contain more than four carbon atoms the substrate on which the microorganism is grown comprises assimilable straight chain carbon compounds having within two carbon atoms of the required number, and particularly the same number of carbon atoms. Thus where a monomer repeat unit contains ten carbon atoms, i.e. C10 monomer, the substrate has to contain at least one assimilable straight chain carbon compound containing eight carbon atoms.

Lageveen et al, *Applied and Environmental Microbiology*, December 1988, pp 2924 to 2932 also employed *Pseudomonas oleovorans* ATCC 29347 to produce a range of polymers comprising monomer repeat units having up to twelve carbon atoms. Lageveen et al cultivated the microorganism on a substrate containing an alkane or alkene having between six to twelve carbon atoms. It is stated by Lageveen et al that the number of carbon atoms in the monomer repeat units having the largest number of carbon atoms always corresponded to the number of carbon atoms contained in the alkane or alkene used in the substrate. It is also disclosed that when the substrate contained an alkane having six carbon atoms, only a small amount of polymer was produced, the polymer consisting of monomer units having six carbon atoms. Furthermore, when the substrate contained an alkene having six carbon atoms no polymer was produced.

In a survey of the accumulation of novel polymers by bacteria, Haywood et al, *Biotechnology Letters*, 1989, Vol. 11, No. 7, pages 471 to 476 essentially confirmed the work of Lageveen et al.

Those assimilable straight chain carbon compounds, used by Brandl et al, and Lageveen et al, can in themselves be difficult, and expensive to produce. Therefore, the microbiologically produced polymers that have been synthesised from such assimilable straight chain carbon compounds also tend to be expensive.

Further, the conversion efficiency of existing microbiological processes for the production of such polymers is also low, thereby adding to the cost of the finished polymer.

SUMMARY OF THE INVENTION

Surprisingly, we have found that certain specific microorganisms can produce and accumulate polymers, other than PHB, when cultivated on a substrate comprising an assimilable carbon source, wherein the assimilable carbon source is one that has hitherto not been convertible to a polymer, other than PHB, by known PHB producing and accumulating microorganisms, thereby enabling the use of assimilable carbon compounds that include ones which are widely available and cheap. Further, we have found while at least one of said specific microorganisms is cultivated in a general microbiological process, wherein a substrate comprising at least one of certain assimilable carbon compounds is provided, polymers are synthesised and accumulated by the microrganism, wherein the polymers comprising monomer repeat units, and the modal number of carbon atoms contained by the monomer repeat units exceeds the number of carbon atoms contained within the assimilable carbon compound by at least 2. Further, we have found that said specific microorganisms can produce and accumulate polymers comprising monomer repeat units having ten carbon atoms when cultivated on a substrate wherein the assimilable carbon compound is glucose.

Accordingly the present invention provides a process for the microbiological production of polymers comprising monomer repeat units, each of said monomer repeat units containing a number of carbon atoms and the modal number of carbon atoms contained by said monomer repeat units being N, said process comprising cultivating a bacterium on a substrate comprising an assimilable carbon compound having fewer than N carbon atoms, wherein the bacterium is either at least one bacterium selected from the group consisting of *Pseudomonas Sp.* NCIMB 40135, *Pseudomonas putida* NCIB 8865, *Pseudomonas putida* NCIB 9571, *Pseudomonas aeruginosa* NCIB 9904, *Pseudomonas aeruginosa* NCIB 8626, and *Pseudomonas fluorescens* NCIB 9520 or has the characteristics of at least one member of said group.

In another aspect the present invention provides novel microbiologically produced polymers comprising monomer repeat units, wherein each of said monomer repeat units contains a number of carbon atoms, and the modal number of carbon atoms contained by said monomer repeat units is at least 10.

Further novel microbiologically produced polymers are also provided, said microbiologically produced polymers comprising monomer repeat units wherein each of said monomer repeat units contains a number of carbon atoms, and
  (a) the modal number of carbon atoms contained by said monomer repeat units is 8;
  (b) those monomer repeat units containing the modal number of carbon atoms comprise at least 40 mol %, preferably at least 50 mol %, of said monomer repeat units; and
  (c) not more than 10 mol %, preferably not more than 1 mol % of said monomer repeat units contain less than the modal number of carbon atoms.

In a further aspect of the present invention a biologically pure culture of a bacterium is provided, said bacterium being capable of synthesising and accumulating polymers and having the characteristics of strain *Pseudomonas sp.* NCIMB 40135.

DETAILED DESCRIPTION OF THE INVENTION

The process of the present invention may be used to prepare microbiologically produced polymers comprising monomer repeat units, wherein each of said monomer repeat units contains a number of carbon atoms, and the modal number of carbon atoms contained by said monomer repeat units, herein denoted as N, is at least six, preferably at least eight, and more particularly is equal to ten.

The assimilable carbon compound provided in the substrate may be any suitable metabolisable carbon compound. Preferably the assimilable carbon compound is a carbohydrate. Particularly the assimilable carbon compound is a sugar compound such as glucose, or a sugar compound that is metabolisable or convertible to glucose, such as sucrose or lactose. Alternatively, the assimilable carbon compound may be acetic acid, succinic acid, lactic acid or glycerol.

Where the modal number of carbon atoms in the monomer repeat units is N, the number of carbon atoms in the assimilable carbon compound is at least N-2, and preferably at least N-4.

Considering the structure of the assimilable carbon compounds from which the microbiologically produced polymers may be derived, it is surprising that the microbiologically produced polymers comprise monomer repeat units having the following general structure

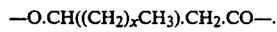

Based on the aforementioned structure, where a monomer repeat unit contains 6 carbon atoms, x is thus equal to 2. Likewise, a monomer repeat unit containing 10 carbon atoms is defined when x is equal to 6. Thus, x is four less than the number of carbon atoms contained by the monomer repeat unit.

The monomer repeat units of the novel polymers of the present invention may be represented by the general structure hereinbefore defined. Thus, the structure of the monomer repeat units containing the modal number of carbon atoms may be represented by equating the parameter x, as hereinabove defined, to N-4.

The novel microbiologically produced polymers, having monomer repeat units with a modal number of carbon atoms of at least 10, may be further defined in that the monomer repeat units having the modal number of carbon atoms particularly comprise at least 70, especially at least 80, and especially at least 90 mol % of those monomer repeat units present.

Additionally, the novel microbiologically produced polymers, having monomer repeat units with a modal number of carbon atoms of at least 10, may also be defined in that particularly less than 5 mol %, and especially less than 1 mol % of the monomer repeat units contain greater than the modal number of carbon atoms.

The novel microbiologically produced polymers may be further defined in that not more than 10 mol % and particularly not more than 2 mol % of the monomer repeat units differ by more than two carbon atoms from the modal number of carbon atoms.

In common with other microorganisms, a microorganism having the characteristics of *Pseudomonas sp.* NCIMB 40135 will reproduce if cultured aerobically, i.e. in the presence of oxygen, in a medium comprising those requirements essential for reproduction, and a substrate comprising an assimilable carbon compound. This reproduction is hereinafter termed growth. Such growth occurs until one or more of the essential requirements for growth are exhausted.

Those requirements essential for growth include various nutrients. These nutrients comprise the following elements, which are normally present in readily assimilable form, normally as water soluble salts: nitrogen, phosphorus, sulphur, potassium, sodium, magnesium, calcium, and iron, together with traces of manganese, zinc and copper.

During the time that growth is sustained, some polymer may be synthesised, and accumulated by the microorganism. Generally, unless the microorganism has been suitably adapted, or selected, so as to exhibit polymer production and accumulation characteristics under growth conditions, the rate, and level, at which polymer is accumulated is low under such growth conditions.

By restricting the amount of at least one of said requirements to which the microorganism has access, the amount of growth may be either very limited in extent or nonexistent. Provided the amount of assimilable carbon compound present in the substrate is sufficient, the microorganism cultivated under these so-called growth limiting conditions will tend to synthesise and accumulate polymer at a rate greater and to a level higher than that found under non-growth limiting conditions.

Preferably therefore the process comprises cultivating the bacterium under growth limiting conditions.

It is particularly preferable to induce polymer accumulation by restricting the supply of one or more of the nutrients as hereinbefore described. The most practical elements to limit are nitrogen, phosphorus, or, less preferably, magnesium, sulphur or potassium. The nitrogen may be conveniently supplied in the form of an ammonium salt, whereas the phosphorus may be conveniently supplied as a phosphate.

Where nitrogen limitation is employed, the substrate is preferably nitrogen free. The amount of assimilable nitrogen required is about 10 to 15% by weight of the desired weight of cells less the weight of the accumulated polymer.

Cultivation of the microorganism may be conducted under conditions of temperature, pH, degree of aeration etc. conventionally used for the microorganism under non-growth limiting conditions. Likewise the amounts of nutrients (other than that of the nutrient used to limit the growth of the microorganism) employed may be those normally provided for growth of the microorganism.

Cultivation of the microorganism preferably comprises a two stage process. In the first stage the microorganism is preferably grown to a certain dry weight per liter, under non-growth limiting conditions on a substrate comprising a readily assimilable carbon compound, such as a carbohydrate, for example glucose. In the second stage at least one nutrient required for growth is limited, such that the growth limiting conditions exist.

The cultivation may be performed as a batch process, such that polymer accumulation will occur as the amount of the nutrient required for growth but not polymer accumulation becomes depleted.

Alternatively, the cultivation may be performed as a continuous process, wherein a stream of culture is removed from the vessel, in which the microorganism is being cultivated, on a continuous or semi-continuous basis. The stream removed from the vessel contains microbial cells in a spent aqueous medium. The spent aqueous medium comprises residual quantities of nutrients and substrate. The flowrate of the stream leaving the vessel corresponds to the rate of addition of fresh aqueous medium to the vessel. The fresh aqueous medium supplied to the vessel contains nutrients and substrate in sufficient amounts to support accumulation of the polymer. Preferably the amount of that nutrient, used to limit the growth of the microorganism, which is fed to the vessel is such that little or none of that nutrient is present in the spent aqueous medium removed from the vessel. Further, it is preferred that the spent aqueous medium is fed to at least one further aerated cultivation stage under batch or continuous or semi-continuous operation, wherein additional polymer accumulation is stimulated by the addition of further substrate to the spent aqueous medium. The levels of nutrients and substrate may be adjusted in the spent aqueous medium after leaving the first cultivation stage such that optimum operation of the overall process is maintained.

In a further alternative, the cultivation of the microorganism may be conducted as a single stage process. In such a process, wherein polymer accumulation is induced by limiting the amount of a nutrient required for growth but not for polymer accumulation, the residence time of the aqueous medium in the vessel is made sufficiently long so as to allow exhaustion of the limiting nutrient, and for polymer accumulation to occur.

In either a single or multistage process, or in a batch or semi-continuous or continuous process a single assimilable carbon compound may be present in the substrate during polymer accumulation, or may be in admixture with other assimilable carbon compounds.

The bacterium capable of synthesising, and accumulating the polymers as hereinbefore described, and in particular those polymers in which the modal number of carbon atoms in said monomer repeat units is ten, is preferably of the genus Pseudomonas. The bacterium is distinguished from related strains by the ability to synthesise and accumulate polymers having monomer repeat units the modal number of carbon atoms in which is ten carbon atoms from an assimilable carbon source consisting of glucose. Particular examples of suitable strains of Pseudomonas are *Pseudomonas Sp.* strain NCIMB 40135, *Pseudomonas putida* strains NCIB 8865 and NCIB 9571, *Pseudomonas aeruginosa* strains NCIB 8626 and 9904, and *Pseudomonas fluorescens* NCIB 9520.

Other strains of bacteria, having similar characteristics to the aforementioned preferred strains, may be used in the process of the present invention. The other strains may inherently have these desired characteristics, or may have acquired these desired characteristics through transference of the necessary genetic information from strains which possess the desired characteristics. The transference of the genetic information, required for the production and accumulation of PHB, between strains of bacteria has previously been disclosed by Schubert et al in the Journal of Bacteriology, 12 (1988) pages 5837 to 5847, and by Slater et al also in the *Journal of Bacteriology*, 10 (1988) pages 4431 to 4436.

*Pseudomonas sp.* NCIMB 40135 was deposited on the 5 May 1989, under the terms and conditions of the Budapest Treaty.

Description of *Pseudomonas sp.* NCIMB 40135.

Morphology

Gram negative rods of approximate size 0.7 um to 1.0 μm×2.0 to 4.0 μm.

Intracellular granules produced.

No spore formation.

Colonial morphology (Lab M Nutrient Agar)—the organism produces round, regular, opaque, smooth, cream-coloured convex colonies. After 2 days growth the diameter was about 2 mm.

Temperature

Optimum growth temperature 25° to 300° C.
No growth at 410° C.

Characteristics

| | |
|---|---|
| Nitrate reduction | − |
| Indole production (from tryptophan) | − |
| Glucose acidification | + |
| Arginine dihydrolase | + |
| Urease | − |
| Esculin hydrolysis | − |
| Gelatin liquefaction | − |
| p-Nitrophenyl-B-D-galactopyranoside hydrolysis | − |
| Glucose assimilation | + |
| Arabinose assimilation | + |
| Mannitol assimilation | + |
| Mannose assimilation | + |
| N-Acetylglocosamine assimilation | + |
| Maltose assimilation | + |
| Gluconate assimilation | + |
| Caprate assimilation | + |
| Adipate assimilation | − |
| Malate assimilation | + |
| Citrate assimilation | + |
| Acetate assimilation | + |
| Phenylacetate assimilation | + |
| Cytochrome oxidase | + |

A specific embodiment of the process of the present invention is further described by reference to the following Examples.

The term nitrogen-limited medium hereinafter refers to a medium in which the amount of nitrogen present in the medium is disproportionate to the amount of the other constituents of the medium. The proportions of nitrogen to other constituents in such a medium is such that a microorganism provided with the medium will utilise the nitrogen and other constituents but will exhaust that nitrogen present, prior to exhausting the other constituents present.

EXAMPLE 1

*Pseudomonas sp.* NCIMB 40135 was aerobically cultured in continuous culture at a pH of 7, and 30° C., in a 2 l chemostat on a nitrogen-limited medium, having the following composition, expressed as per liter of distilled water.

| | |
|---|---|
| $MgSO_4.7H_2O$ | 0.4 (g) |
| $K_2SO_4$ | 0.4 (g) |
| $Na_2SO_4$ | 0.025 (g) |
| $FeSO_4.7H_2O$ | 0.025 (g) |
| $H_3PO_4$ (85% w/w) | 1.0 (ml) |
| Glucose | 30.0 (g) |
| $(NH_4)_2SO_4$ | 0.62 (g) |
| Trace element solution | 10.0 (ml) |

The trace element solution had the following composition, per liter of distilled water:

| | |
|---|---|
| $MnSO_4.4H_2O$ | 0.406 (g) |
| $ZnSO_4.7H_2O$ | 0.440 (g) |
| $CuSO_4.5H_2O$ | 0.078 (g) |
| $CaCl_2.2H_2O$ | 7.34 (g) |

The nitrogen-limited medium was fed through the chemostat so as to achieve a dilution rate of 0.1 $hr^{-1}$.

The bacteria were harvested by centrifugation, washed with water and freeze-dried. The polymer content of the whole bacteria was determined by gas chromatography of the methyl-3-hydroxyacids produced by methanolysis. Analysis showed that the the cells contained 5.2% w/w of polymer.

EXAMPLE 2

The procedure of Example 1 was repeated with the exception that the dilution rate was decreased to 0.035 $hr^{-1}$. Subsequent analysis of the polymer content of the cells showed there to be 21.4% w/w of polymer present.

EXAMPLE 3

The procedure of Example 1 was repeated with the exception that the aeration of the culture was decreased such that the level of dissolved oxygen tension was 1% that of the air saturation value. Subsequent analysis of the polymer content of the cells showed there to be 10.4% w/w of polymer present.

EXAMPLE 4

In a comparative example, the procedure of Example 3 was repeated with the exception that the aeration rate was still further decreased to the extent that the culture was oxygen-limited. This was established when unused nitrogen was detectable in the culture. Subsequent analysis of the cells showed there to be no polymer present.

EXAMPLE 5

In a further example of the process of the present invention, *Pseudomonas sp.* NCIMB 40135 was aerobically grown in shake-flask culture at a pH of 7, and 300° C., in a 1 l flask containing 200 ml of a medium having the following composition, expressed as per liter of distilled water.

| | |
|---|---|
| $MgSO_4.7H_2O$ | 0.4 (g) |
| $FeSO_4.7H_2O$ | 0.025 (g) |
| $K_2HPO_4$ | 7.6 (g) |
| $NaH_2PO_4$ | 6.24 (g) |
| Glucose | 10.0 (g) |
| $(NH_4)_2SO_4$ | 7.0 (g) |
| Trace element solution | 10.0 (ml) |

After 24 hours the bacteria were aseptically harvested by centrifugation, and transferred to 200 ml of fresh medium that was nitrogen deficient, i.e. did not contain any $(NH_4)_2SO_4$. The bacteria were then aerobically cultivated in shake-flask culture for a further 24 hours. The bacteria were then harvested by centrifugation, washed and freeze dried. The polymer content of the cells was determined in the same manner as in Example 1, and was shown to be 4.0% w/w.

EXAMPLE 6

The procedure of Example 5 was repeated with the exception that the glucose was replaced with sodium acetate, at a concentration of 10 g.l$^{-1}$. Subsequent analysis of the polymer content of the cells showed there to be 6.4% w/w of polymer present.

EXAMPLE 7

The procedure of Example 6 was repeated. Subsequent analysis of the polymer content of the cells showed there to be 4.6% w/w of polymer present.

EXAMPLE 8

The procedure of Example 5 was repeated with the exception that the glucose was replaced with glycerol, at a concentration of 10 g.l$^{-1}$. Subsequent analysis of the polymer content of the cells showed there to be 4.7% w/w of polymer present.

EXAMPLE 9

The procedure of Example 5 was repeated with the exception that the glucose was replaced with lactate, at a concentration of 10 g.l$^{-1}$. Subsequent analysis of the polymer content of the cells showed there to be 8.5% w/w of polymer present.

EXAMPLE 10

The procedure of Example 5 was repeated with the exception that the glucose was replaced with succinate, at a concentration of 10 g.l$^{-1}$. Subsequent analysis of the polymer content of the cells showed there to be 1.3% w/w of polymer present.

EXAMPLE 11

The procedure of Example 5 was repeated with the exception that the glucose was replaced with fructose, at a concentration of 10 g.l$^{-1}$. Subsequent analysis of the polymer content of the cells showed there to be 16.4% w/w of polymer present.

EXAMPLE 12

The procedure of Example 5 was repeated with the exception that the glucose was replaced with gluconate, at a concentration of 10 g.l$^{-1}$. Subsequent analysis of the polymer content of the cells showed there to be 16.5% w/w of polymer present.

EXAMPLE 13

The procedure of Example 12 was repeated with the exception that the strain *Pseudomonas sp.* NCIMB 40135 was replaced with strain *Pseudomonas putida* NCIB 8865. Subsequent analysis of the polymer content of the cells showed there to be 25.8% w/w of polymer present.

EXAMPLE 14

The procedure of Example 12 was repeated with the exception that the strain *Pseudomonas sp.* NCIMB 40135 was replaced with strain *Pseudomonas putida* NCIB 9571. Subsequent analysis of the polymer content of the cells showed there to be 8.9% w/w of polymer present.

EXAMPLE 15

The procedure of Example 12 was repeated with the exception that the strain *Pseudomonas sp.* NCIMB 40135 was replaced with strain *Pseudomonas aeruginosa* NCIB 9904. Subsequent analysis of the polymer content of the cells showed there to be 2.5% w/w of polymer present.

EXAMPLE 16

The procedure of Example 12 was repeated with the exception that the strain *Pseudomonas sp.* NCIMB 40135 was replaced with strain *Pseudomonas aeruginosa* NCIB 8626. Subsequent analysis of the polymer content of the cells showed there to be 1.5% w/w of polymer present.

EXAMPLE 17

The procedure of Example 12 was repeated with the exception that the strain *Pseudomonas sp.* NCIMB 40135 was replaced with strain *Pseudomonas fluorescens* NCIB 9520. Subsequent analysis of the polymer content of the cells showed there to be 0.2% w/w of polymer present.

Further analysis of the polymers produced according to the microbiological processes as described in the aforementioned Examples 1 to 3, and 5 to 17, showed the polymers therein to have the following compositions.

| Ex. No. | Strain (NCIB) | Carbon Source C Atoms | Polymer % w/w | Mol % Monomer in Polymer | | |
|---|---|---|---|---|---|---|
| | | | | C6 | C8 | C10 |
| 1 | 40135 | 6 | 5.2 | 1 | 14 | 85 |
| 2 | " | 6 | 21.4 | 1 | 19 | 80 |
| 3 | " | 6 | 10.4 | 2 | 15 | 83 |
| 5 | " | 6 | 4.0 | 0 | 17 | 83 |
| 6 | " | 2 | 6.4 | 0 | 17 | 83 |
| 7 | " | 2 | 4.6 | 0 | 15 | 85 |
| 8 | " | 3 | 4.7 | 0 | 10 | 90 |
| 9 | " | 3 | 8.5 | 0 | 15 | 85 |
| 10 | " | 4 | 1.3 | 0 | 53 | 47 |
| 11 | " | 6 | 16.4 | 0 | 17 | 83 |
| 12 | " | 6 | 16.5 | 0 | 20 | 80 |
| 13 | 8865 | 6 | 25.8 | 0 | 15 | 85 |
| 14 | 9571 | 6 | 8.9 | 0 | 24 | 76 |
| 15 | 9904 | 6 | 2.5 | 0 | 0 | 100 |
| 16 | 8626 | 6 | 1.5 | 0 | 15 | 85 |
| 17 | 9520 | 6 | 0.2 | 0 | 0 | 100 |

We claim:
1. A process for the microbiological production of polyester containing a modal number of repeat units having the formula

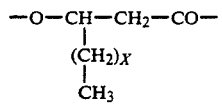

wherein
X is 4 or 6, said process comprising cultivating, under aerobic conditions and pH of about 7, at least one bacterium on a substrate comprising an assimilable carbon compound selected from glucose, fructose, acetate, succinate, lactate, gluconate and glycerol; said bacterium being selected from the group consisting of *Pseudomonas sp.* NCIMB 40135, *Pseudomonas putida* NCIB 8865, *Pseudomonas putida* NCIB 9751, *Pseudomonas aeruginosa* NCIB 9904, *Pseudomonas aeruginosa* NCIB 8626, *Pseudomonas fluorescens* NCIB 9520, and recovering the polyester from the cultivation.

2. A process according to claim 1 in which the bacterium is *Pseudomonas sp.* NCIMB 40135.

* * * * *